United States Patent [19]

Tabak

[11] Patent Number: 4,985,203
[45] Date of Patent: Jan. 15, 1991

[54] CONVERSION SYSTEM FOR CONVERTING OXYGENATES TO HYDROCARBONS

[75] Inventor: Samuel A. Tabak, Wenonah, N.J.

[73] Assignee: Mobil Oil Corporation, New York, N.Y.

[21] Appl. No.: 11,666

[22] Filed: Feb. 5, 1987

Related U.S. Application Data

[63] Continuation-in-part of Ser. No. 779,346, Sep. 23, 1985, Pat. No. 4,654,453.

[51] Int. Cl.$^5$ .......................... B01J 8/24; C10G 11/18
[52] U.S. Cl. ........................................ 422/190; 208/78;
208/80; 422/148; 422/200; 422/201; 422/211;
585/303; 585/318; 585/322; 585/323; 585/408;
585/413; 585/415; 585/469; 585/475
[58] Field of Search ............... 422/190, 200, 201, 211,
422/148; 585/315, 322, 323, 407, 408, 413, 415,
475, 503; 208/78, 80

[56] References Cited

U.S. PATENT DOCUMENTS

| | | |
|---|---|---|
| 3,969,426 | 7/1976 | Owen et al. . |
| 4,025,576 | 5/1977 | Chang et al. . |
| 4,048,250 | 9/1977 | Garwood et al. . |
| 4,105,707 | 8/1978 | Little et al. . |
| 4,404,414 | 9/1983 | Penick et al. .................. 585/469 |
| 4,423,274 | 12/1983 | Daviduk et al. . |
| 4,433,185 | 2/1984 | Tabak ................................. 585/312 |
| 4,433,188 | 2/1984 | Hoelderich et al. . |
| 4,444,988 | 4/1984 | Capsuto et al. . |
| 4,499,314 | 2/1985 | Seddon et al. . |
| 4,506,106 | 3/1985 | Hsia et al. . |
| 4,523,046 | 6/1985 | Gould et al. . |
| 4,547,613 | 10/1985 | Garwood et al. . |
| 4,579,999 | 4/1986 | Gould et al. . |

Primary Examiner—Robert J. Warden
Assistant Examiner—Jill Johnston
Attorney, Agent, or Firm—Alexander J. McKillop; Charles J. Speciale; L. G. Wise

[57] ABSTRACT

Aliphatic oxygenates are converted to high octane gasoline by an integrated reactor system wherein three reaction zones are utilized. In a first reaction zone the oxygenates are directly converted to gasoline and an isobutane by-product. In a second reaction zone oxygenates are dehydrated to an intermediate product comprising $C_3$-$C_4$ olefins, which are then further reacted with the isobutane by-product in a third reaction zone to yield a gasoline alkylate. Ethylene-containing vapors may be separated from the second reaction zone and recycled to the first reaction zone for further processing.

5 Claims, 2 Drawing Sheets

CONVERSION SYSTEM FOR CONVERTING OXYGENATES TO HYDROCARBONS

REFERENCE TO COPENDING APPLICATION

This application is a continuation in part of U.S. patent application Ser. No. 779,346, filed Sept. 23, 1985, now U.S. Pat. No. 4,654,453.

BACKGROUND OF THE INVENTION

This invention relates to an integrated process reactor system for converting oxygenates such as methanol and dimethyl ether (DME) to liquid hydrocarbons. The oxygenate feedstock is contacted with a zeolite catalyst in a reaction zone to distillate and/or gasoline through an intermediate olefinic material.

It is known to contact an oxygenate feedstock with a dehydration catalyst to produce lower olefins, which may be employed as starting materials for producing gasoline. The $C_3$–$C_4$ olefins are mixed with isobutane and directed to an acid alkylation reaction zone to yield a valuable alkylate gasoline.

The following patents are examples of related prior art. Their disclosures are incorporated herein by this reference to them.

U.S. Pat. No. 3,972,958 (Garwood et al) discloses a process for converting coal to high octane gasoline which includes the step of alkylating the $C_3$–$C_4$ olefins with isobutane.

U.S. Pat. No. 4,211,885 (Banks) discloses a process for producing high octane gasoline which includes the step of alkylating a butenes stream with isobutane.

The foregoing patents do not teach the concept of providing an alkylation unit with a feedstock derived from a combination of an MTG (methanol to gasoline) reactor and an MTO (methanol to olefin) reactor.

In a typical fixed-bed MTG process relatively large amounts of isobutane are produced, eg., about 8% by weight of hydrocarbons product. In the past, it has been the practice to recover the isobutane fraction without an immediate upgrading step. In fluidized bed MTG operations, isobutane production may be balanced with $C_3$–$C_4$ olefin production to provide a stoichiometric ratio for separation and upgrading, or excess isobutane byproduct may be made.

SUMMARY OF THE INVENTION

It has been discovered that improved yield of high octane gasoline may be obtained by providing a small MTO (methanol to olefin) conversion unit and an alkylation reaction unit in conjunction with a large-scale MTG (methanol to gasoline) reaction zone. In the present reactor system, isobutane from the MTG process may be contacted with $C_3$–$C_4$ olefins, derived from the MTO unit, to produce gasoline in an alkylation zone. The overall yield of high octane gasoline from oxygenate conversion is significantly increased. In a further improvement, the ethylene-containing vapors are separated from the other products of the MTO process and recycled to the MTG reaction zone.

In the preferred embodiment a process reactor system is provided for converting oxygenate feedstock to liquid hydrocarbons. The system includes first reactor means for converting oxygenate feedstock predominantly to gasoline range hydrocarbons in a first reactor zone in contact with acid shape selective, medium pore zeolite catalyst thereby producing a minor amount of excess isobutane and means for separating isobutane from the first reactor effluent. The second reactor means converts oxygenate feedstock predominantly to $C_2$–$C_5$ lower olefins in a second reactor zone in contact with zeolite catalyst, while maintaining sufficient production of $C_3^+$ olefins in the second reactor zone to react with excess isobutane produced in the first reactor zone. The interstage separator provides means for separating an ethene rich stream from the second reactor olefinic effluent, along with means for passing the ethene-rich stream to the first reactor zone for further conversion of ethene to heavier hydrocarbons. The alkylation reactor means alkylates the isobutane with $C_3^+$ olefins in a third reactor zone in contact with an acid catalyst.

DESCRIPTION OF PREFERRED EMBODIMENTS

Figure 1:
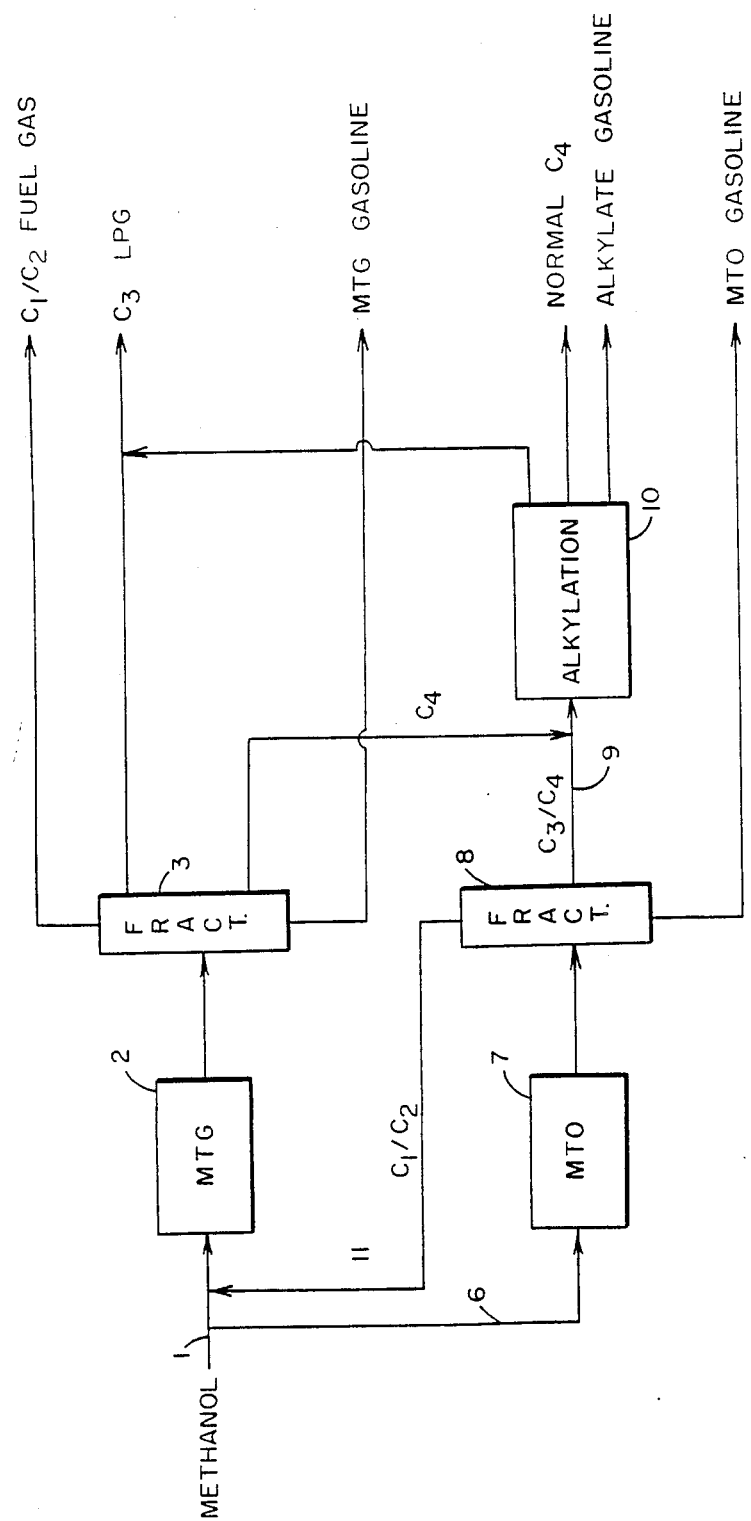
FIG. 1 is a process flow diagram depicting the multistage integrated system.

The feedstock for both the MTG and the MTO processes is lower molecular weight oxygenated organic compound(s). Examples of such compounds are $C_1$–$C_4$ aliphatic alcohols, ethers, esters, ketones, and aldehydes. Since methanol or its ether derivative (DME) are industrial commodities available from synthesis gas or the like, these materials are utilized in the description herein as preferred starting materials. It is known in the art to partially convert oxygenates by dehydration, as in the catalytic reaction of methanol over gamma-alumina to produce DME intermediate. Typically, a mixture ($CH_3OH + CH_3$—$O$—$CH_3 + H_2O$) is produced by partial dehydration. This reaction takes place in both conversion of methanol to gasoline (MTG) and methanol to lower olefins (MTO).

DESCRIPTION OF CATALYSTS

The zeolite catalysts preferred for use in both MTO and MTG processes herein include the mediuim pore metallosilicate zeolites. Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The MTG catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity (alpha value) of about 10–250, preferably about 15 to 80 based on total catalyst weight. In a fluidized bed reactor the coked catalyst may have an apparent activity (alpha value) of about 10 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, ZSM-38, and ZSM-48. Aluminosilicate ZSM-5 is disclosed in U.S. Pat. No. 3,702,886 and U.S. Pat. No. Re. 29,948. Other zeolites are disclosed in U.S. Pat. Nos. 3,709,979; 3,832,449; 4,076,979; 3,832,449; 4,076,842; 4,016,245 and 4,046,839; 4,414,423; 4,417,086; 4,465,889; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity and aromatization characteristics. A typical zeolite catalyst component having Bronsted acid sites may consist essentially of aluminosilicate ZSM-5 zeolite with 5 to 95 wt. % silica and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. The zeolite may include a one or more metals of group IB, IIB, IIIB, VA, VIA or VIIIA of the Periodic Table (IUPAC) Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to 2 microns or more. ZSM-5 type catalysts are particularly advantageous because the same material may be employed for dehydration of methanol to DME, conversion to lower olefins and ethylene conversion.

DESCRIPTION OF REACTOR SYSTEMS

Referring to FIG. 1 of the drawing, the process feedstock 1, consisting essentially of methanol and/or DME, for instance, is directed via conduit 1 to a typical primary oxygenate converstion reactor unit, such as a fluidized or fixed-bed MTG catalytic reactor 2. A fixed bed reactor system will be discussed initially. Oxygenate feedstock is converted predominantly to gasoline range hydrocarbons in this first reactor zone, in contact with ZSM-5 type zeolite catalyst, thereby producing a minor amount of isobutane. The effluent from reactor 2 is conducted to frationation system 3 where it is separated into a gasoline fraction, an isobutane-rich $C_4$ stream, a $C_3$ liquified petroleum gas (LPG) fraction, and an overhead stream of $C_1$-$C_2$ fuel gas.

A portion of the process feedstock (methanol and/or DME) is directed via conduit 6 to a catalytic MTO reactor 7. Effluent from reactor 7 is conducted to a fractionation system 8 where it is separated into a gasoline fraction, an ethane-rich fraction and a $C_3$-$C_4$ olefin fraction. The $C_3$-$C_4$ olefin stream from fractionator 8 is directed via conduit 9 to acid alkylation unit 10, where it is combined with the isobutane rich $C_4$ stream to alkylate the isobutane with $C_3$-$C_4$ olefins in the third reactor zone in contact with an acid catalyst.

By converting oxygenate feedstock predominantly to $C_2$-$C_5$ lower olefins in the second reactor zone 7 in contact with zeolite catalyst, separating an ethene rich stream 11 from the second reactor olefinic effluent and further converting the ethene to heavier hydrocarbons in the first reactor zone 2, a balanced multistage process is achieved.

The MTO process may be optimized to produce at least 30% $C_3$-$C_4$ olefins by employing fluid bed primary stage conditions in the temperature range of about 425° C. to 550° C., a pressure range of about 100 to 800 kPa and weight hourly space velocity range of about 0.5 to 3.0 based on ZSM-5 type catalyst (alpha=1–50) and methanol equivalent in the primary stage feedstock. Suitable equipment and operating conditions are described in U.S. patent application Ser. No. 687,045 filed 28 Dec. 1984, now U.S. Pat. No. 4,547,616, incorporated herein by reference.

The MTG process unit may be a fixed bed type, as disclosed in U.S. Pat. Nos. 3,894,107; 3,928,483; 3,931,349; 4,048,250; etc. It is known to recycle ethene in the production of aromatic gasoline from methanol over zeolites (U.S. Pat. No. 3,998,899, Daviduk). In a fluidized bed plant for converting methanol to lower olefins and gasoline, recycle of ethylene at a rate of 2.5 part by weight by 100 parts $CH_2$ equivalent in the feedstock methanol provides a product yield that is substantially the same, as shown in Table 1. These continuous runs are conducted at the same conditions.

TABLE I

| | Hydrocarbon Product Yield, Wt % | |
|---|---|---|
| Component | Without Recycle | With ethene Recycle |
| $C_1$ | 0.8 | 0.8 |
| $C_2$ | 0.3 | 0.3 |
| $C_2=$ | 2.5 | 2.7 |
| $C_3$ | 4.4 | 4.5 |
| $C_3=$ | 4.6 | 4.5 |
| $nC_4$ | 2.1 | 2.1 |
| $iC_4$ | 10.8 | 10.4 |
| $C_4=$ | 5.4 | 5.1 |
| $C_5+$ (Gasoline) | 69.1 | 69.6 |
| Total | 100.0 | 100.0 |

T = 407° C, P = 400 kPa, WHSV = 2.65⁻ (based on HZSM-5 catalyst)

In a typical fixed-bed MTG process, large amounts of isobutane are produced, typically 8 wt % of hydrocarbon. However, there is generally not sufficient $C_3/C_4$ olefins produced (0.4 wt % of hydrocarbons) to consume the isobutane by acid alkylation.

The present invention provides MTO and alkylation units in conjunction with a fixed-bed or fluidized bed MTG plant, wherein the MTO reactor is sized to produce sufficient $C_3/C_4$ olefins to react with the excess MTG isobutane, thus maximizing $C_5+$ liquid yield. For a balanced process, the propylene and butylene produced in the MTO unit together with that produced in the main MTG reactor should be approximately stoichiometric to the excess isobutane produced in the plant. In addition to producing alkylate from $C_3=/C_4=$olefin, the plant can be operated to produce $C_5=/i-C_5$ alkylate for use as jet fuel. For a gas-based synthetic fuels complex, gas field isobutane or butane isomerization can provide additional isobutane for feed.

Overall the producton of MTO gasoline plus alkylate will increase blended gasoline pool octane because of their high component octanes. Also, by reacting the isobutane out of the $C_4$ plant product, a relatively pure normal butane stream is produced for gasoline pressurization. This will increase gasoline yield since normal butane has a lower vapor pressure than isobutane. Also, the $C_1$-$C_2$ off gas from MTO can be routed to the MTG unit to react $C_2=$ to gasoline. This will eliminate the need for cryogenic separation required to separate ethylene for recycle to the MTO unit.

FLUIDIZED BED MTG OPERATION

Figure 2:
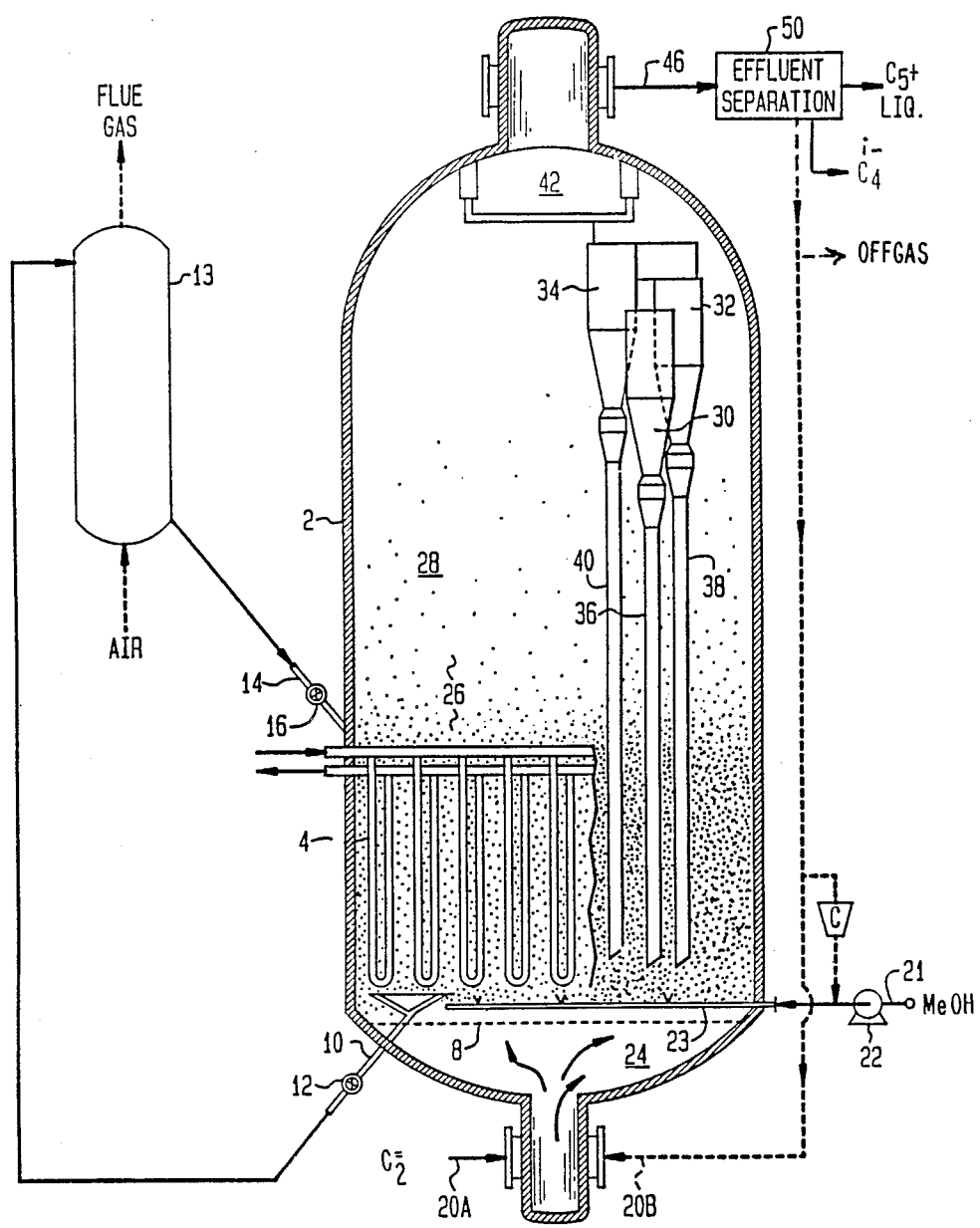
FIG. 2 is a vertical cross section view of a typical fluidized bed MTG reactor useful in the present system.

A suitable fluidized bed reactor for converting methanol feedstock to predominantly $C_5+$ gasoline range hydrocarbons is depicted in vertical cross section in FIG. 2 of the drawing. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 95 wt %, of the methanol/DME feedstock. In the description of fluidized bed embodiments, a 25% H-ZSM-5 catalyst calcined with 75% silica-alumina matrix binder is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 40 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds.

The fluidized bed MTG process may be tolerant of a wide range of lower aliphatic hydrocarbons. Total fresh and recycled feedstocks may contain 0 to 50 wt. % $C_1$-$C_6$ lower aliphatic hydrocarbons, which may be converted to heavier hydrocarbons The desired MTG products are $C_4$ to $C_9$ hydrocarbons, which will ordinarily comprise at least 50% of the recovered product. While aliphatics may be a predominant fraction of the $C_4+$ reaction effluent; it may be desirable to upgrade the feedstock to high octane gasoline containing aromatics, preferably at least 5% $C_6$-$C_8$ aromatics (BTX).

The reaction severity conditions can be controlled to optimize yield of $C_4$-$C_9$ hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) can be maintained from high activity values greater than 100 or significantly lower values under steady state operation by controlling catalyst deactivation and regeneration rates. Typical MTG fluidized bed reaction conditions can be obtained in U.S. Pat. No. 4,513,160 to Avidan and Kam, incorporated herein by reference.

Upgrading of olefins by methanol hydrogen contributors in fluidized bed cracking and oligomerization units is taught by Owen et al in U.S. Pat. No. 4,090,949. This technique is particularly useful for operation with a fluidized bed MTG unit to increase overall production of liquid product and isobutane.

Referring now to FIG. 2, a reactor vessel 2 is shown provided with heat exchange tube means 4. There may be several separate heat exchange steam generating tube bundles so that temperature control can be separately exercised over different portions of the fluid catalyst bed. The bottoms of the tubes are spaced above a feed distributor grid 8 sufficiently to be free of jet action by the charged gas (eg-ethene) passing through the small diameter holes in the grid 8. Although depicted without baffles, the vertical reaction zone can contain open end tubes above the grid for maintaining hydraulic constraints, as disclosed in U.S. Pat. No. 4,251,484 (Daviduk and Haddad). Optionally, a variety of horizontal baffles may be added to limit axial mixing in the reactor. Heat released from the reaction can be controlled by adjusting feed temperature in a known manner. Much of the reaction heat can be removed by feeding cold liquid into the reactor. In reactor configuration shown the heat exchanger tubes can function as dummy tubes to limit mixing in the reactor.

Provision is made for withdrawing catalyst from above grid 8 as by conduit means 10 provided with flow control valve 12 for passage to catalyst regeneration in vessel 13 where coked catalyst particles are oxidatively regenerated in contact with air or other regeneration gas at high temperature. Provision is also made for passing the partially regenerated catalyst to the reactor fluid bed of catalyst by conduit means 14 provided with flow control valve 16. The regenerated catalyst is charged to the catalyst bed sufficiently below the upper interface to achieve good mixing in the fluid bed. Since the flow of regenerated catalyst passed to the reactor is small, hot regenerated catalyst does not upset the temperature constraints of the reactor operations in a significant amount.

Initial fluidization is achieved by forcing lift gas upwardly through the catalyst. In the preferred embodiment, ethene-rich light olefinic gas with or without diluent or other recycle may be charged through inlet port 20A at a bottom portion of the reactor in open communication with chamber 24 beneath grid 8. Pressurized oxygenate feedstock is introduced above reactant distributor grid 8 via supply conduit 21, pump 22 and distributor conduit 23 to one or more spray nozzle means. The liquid is dispersed into the bed of catalyst thereabove at a velocity sufficient to form a generally upwardly flowing suspension of atomized liquid reactant with the catalyst particles and lift gas.

Advantageously, the liquid oxygenate reactant feed is injected into the catalyst bed by atomizing the pressurized liquid feedstream to form readily dispersible liquid particles having an average size of 50 microns or less. This contributes to rapid vaporization of the liquid at process pressure. Exothermic conversion provides sufficient heat to vaporize the liquid quickly, thus avoiding liquid phase reactions.

In order to prevent premature non-catalytic reaction of methanol, it is desirable to maintain reactant liquid feedstream temperature below feedstock decomposition temperature until injection into the fluidized bed. Appropriate thermal insulation or quenching of the feedstream to the injection point can largely prevent coke formation in the liquid phase prior to catalysis. Thermal isolation of the liquid oxygenate feedstream from the hot reaction medium in the reaction vessel can be achieved by applying to the liquid feed conduit a layer of thermal insulation, such as a ceramic shield or the like. Jacketed conduits with heat adsorbing fluid may also be suitable. Atomization of the pressurized liquid oxygenate feedstream can be achieved by known techniques, such as liquid spray nozzles, motive gas, ultrasonics, etc.

A plurality of sequentially connected cyclone separator means 30, 32 and 34 provided with diplegs 36, 38 and 40 respectively are positioned in an upper portion of the reactor vessel comprising dispersed catalyst phase 28. The product effluent separated from catalyst particles in the cyclone separating system then passes to a plenum chamber 42 before withdrawal via conduit 46, operatively connected with effluent separation system 50. The product effluent is cooled and separated to recover an isobutane stream, $C_5+$ liquid hydrocarbons, gaseous recycle or offgas, along with any byproduct water or catalyst fines carried over. A portion of the light gas effluent fraction may be recycled by compressing to form a motive gas for the liquid feed or via recycle conduit 20B for use as supplemental lift gas. The recovered gasoline range product comprising $C_5+$ aliphatics and/or aromatics, and naphthenes is thereafter processed as required to provide a desired gasoline or higher boiling product.

A typical turbulent bed may have a catalyst carryover rate up to about 1.5 times the reaction zone inventory per hour. If the fraction of fines becomes large, a portion of the carryover can be removed from the system and replaced by larger particles. It is feasible to have a fine particle separator, such as a cyclone disposed within the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a high operating temperature sintered metal filter.

MTO REACTOR OPERATION

In a preferred embodiment, the MTO reactor is optimized to produce propylene and butylene for alkyation. This can be achieved with a fluidized bed reactor, as described in U.S. Pat. No. 4,547,616 to Avidan et al, incorporated herein by reference. Recovery of ethylene from the MTO reactor system effluent is disclosed in U.S. Pat. No. 4,543,999 by Gould et al.

ALKYLATION REACTION

The alkylation process employed herein is a well known industrial technique for reacting alkenes with tertiary alkanes (isoparaffins), such as isobutane, isopentane, isohexane, etc. The resulting product is a $C_7+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21-41 MPa (3000-6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular acid catalysts involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylkation of isobutane with propene are mainly 2,3- and 2,4-dimethylpentane. Propene is alkylated preferably as a component of a $C_3$–$C_4$ fraction. HF catalysts for alkylation of isobutane with 1- and 2-butenes give both dimethylhexanes and trimethylpentanes. The product obtained from alkylation of isobutane with isobutylene at low temperature (e.g., −25° C.) with hydrogen fluoride is 2,2-4-trimethylpentane.

During use the acid catalysts may become diluted with byproduct hydrocarbons and as a result decrease in activity. Sulfuric acid concentrations are maintained at about 90%. Hydrogen fluoride concentrations of 80–90% are common, although the optimum concentration depends on the reaction temperature and reactor geometry. Operation below these acid concentrations generally causes incomplete conversion or polymerization. With sulfuric acid, the product quality is improved when temperatures are reduced to the range of 0°–10° C. Cooling requirements are obtained by low temperature flashing of unreacted isobutane. With hydrogen fluoride, the reaction process is less sensitive to temperature, and temperatures of 0°–40° C. can be used. Some form of heat removal is essential because the heat of reaction is approximately $14 \times 10^5$ J/Kg (600 Btu/lb) of butenes converted. Typically the elevated pressure for alkylation by these acid catalyst is about 1500 to 3000 kPa (200–300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive $i\text{-}C_4H_8$ readily alkylates to give an excellent product. The alkylation of pure $1\text{-}C_4\text{-}H_8$ by itself proceeds with considerable isomerization of the $1\text{-}C_4\text{-}H_8$ to $2\text{-}C_4\text{-}H_8$ followed by alkylarion to give a highly branced product. The presence of $i\text{-}C_4H_8$ accelerates the alkylation reaction and allows less time for olefin isomerization. Consequently, the reaction produces an alkylate with a lowered antiknock value. For the sulfuric acid system, isobutane tends to oligomerize and causes other side reaction products of inferior quality; but the isomerization of 1-$C_4$-$H_8$ to 2-$C_4$-$H_8$ proceeds more completely, thereby favoring formation of superior products. Thus for mixed olefin feeds such as described above, the two factors with both catalyst systems counteract each other to provide products of similar antiknock properties.

The olefin-producing MTO process will simultaneously generate isobutane, but the amount may be insufficient to alkylate the coproduced olefins. A suitable outside source of isobutane is natural gas or a by-product of methanol-to-gasoline (MTG) processes.

Suitable alkylation processes are described in U.S. Pat. No. 3,879,489 (Yurchak et al), 4,115,471 (Kesler), 4,377,721 (Chester) and in the Kirk-Othmer Encylcopedia of Chemical Technology, Vol. 2, pp. 50–58 (3rd Ed., 1978) John Wiley & Sons, incorporated herein by reference.

The combined process units are an effective means for converting oxygenated organic compounds, such as methanol, DME, lower aliphatic ketones, aldehydes, esters, etc. to valuable hydrocarbon products. Thermal intergration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

I claim:

1. A process reactor system for converting oxygenate feedstock to liquid hydrocarbons comprising:

first reactor means for converting oxygenate feedstock predominantly to gasoline range hydrocarbons in a first reactor zone, in contact with acid shape selective, medium pore zeolite catalyst thereby producing a minor amount of excess isobutane;

means for separating isobutane from the first reactor effluent;

second reactor means for converting oxygenate feedstock predominantly to $C_2$–$C_5$ lower olefins in a second reactor zone in contact with zeolite catalyst, while maintaining sufficient production of $C_3$+olefins in the second reactor zone to react with excess isobutane produced in the first reactor zone;

means for separating an ethene rich stream from the second reactor olefinic effluent;

means for passing the ethene-rich stream to the first reactor zone for further conversion of ethene to heavier hydrocarbons; and alkylation reactor means for alkylating the isobutane with $C_3$+ olefins in a third reactor zone in contact with an acid catalyst.

2. The system of claim 1 wherein catalyst in said first and second zones comprises acid ZSM-5.

3. The system of claim 2 wherein the first reactor comprises a fixed bed of catalyst whereby isobutane is produced in the amount of about 5 to 10 weight percent of hydrocarbons therein.

4. The system of claim 1 wherein the first reactor comprises a fluidized bed of fine catalyst particles maintained in a vertical reaactor shell;

means for introducing recycled ethylene below the catalyst bed for upward flow therethrough.

5. The system of claim 4 further comprising means for introducing oxygenate feedstock to the first reaction zone by pumping liquid feedstock for injection therein.

* * * * *